(12) United States Patent
Raederstorff et al.

(10) Patent No.: US 8,680,147 B2
(45) Date of Patent: Mar. 25, 2014

(54) COMPOSITIONS

(75) Inventors: Daniel Raederstorff, Flaxlanden (FR); Goede Schueler, Weil am Rhein (DE); Joseph Schwager, Basel (CH); Christof Wehrli, Witterswil (CH)

(73) Assignee: DSM IP Assets B.V., Heerlen (NL)

( * ) Notice: Subject to any disclaimer, the term of this patent is extended or adjusted under 35 U.S.C. 154(b) by 1075 days.

(21) Appl. No.: 12/515,332

(22) PCT Filed: Nov. 21, 2007

(86) PCT No.: PCT/EP2007/010076
§ 371 (c)(1),
(2), (4) Date: Nov. 12, 2009

(87) PCT Pub. No.: WO2008/061724
PCT Pub. Date: May 29, 2008

(65) Prior Publication Data
US 2010/0056634 A1    Mar. 4, 2010

(30) Foreign Application Priority Data
Nov. 24, 2006 (EP) ..................... 06024382

(51) Int. Cl.
*A61K 31/192* (2006.01)
*C07C 63/33* (2006.01)
*A61P 19/02* (2006.01)

(52) U.S. Cl.
USPC ......................................... 514/569; 562/492

(58) Field of Classification Search
None
See application file for complete search history.

(56) References Cited

U.S. PATENT DOCUMENTS 6,492,429 B1 * 12/2002 Graus et al. .................. 514/688

FOREIGN PATENT DOCUMENTS

| JP | 2003-102444 | 4/2003 | | |
|---|---|---|---|---|
| JP | 2004-532212 | 10/2004 | | |
| JP | 2005-15440 | 1/2005 | | |
| WO | WO 02/080682 | 10/2002 | | |
| WO | WO 2005/025586 | 3/2005 | | |
| WO | WO 2006/041256 | * | 4/2006 | ............... A61K 7/48 |
| WO | WO 2006/053415 | 5/2006 | | |

OTHER PUBLICATIONS

Djarmati in Collect. Czech. Chem. Comm. 18, 1919-1924 (1993).*
Hilaire in US Pharm. 2006;5:49-55.*
Wandel et al. in the British Medical Journal, 2010; 341:c4675, 1-9.*
Sawitzke et al. in Arthritis & Rheumatism, vol. 58, Issue 10, pp. 3183-3191, Oct. 2008.*
Stefanovic-Racic et al.in Arthritis and Rheumatism 37, 7, 1994, 1062-1069.*
Richheimer et al. in JAOCS 73, 507-514 (1996).*
Chan et al. in Cancer Letters 96, (1995) 23-29.*
International Search Report for PCT/EP2007/010076, mailed Jun. 10, 2008.
Written Opinion of the International Searching Authority for PCT/EP2007/010076, mailed Jun. 10, 2008.
Takeda, et al., "Chemical constituents of an Uzbek medicinal plant, *Perovskia scrophularifolia*", J. Nat Med., vol. 61, (2007), pp. 84-85.
Espacenet Bibliographic data for JP10036282, Feb. 10, 1998, 1 page.
Oluwatuyi, M. et al., "Antibacterial and Resistance Modifying Activity of *Rosmarinus officinalis*", Phytochemistry, vol. 65, No. 24, (Dec. 1, 2004), pp. 3249-3254.
Reuter, Juliane et al., "Sage Extract Rich in Phenolic Diterpenes Inhibits Ultraviolet-Induced Erythema in Vivo", Planta Med., vol. 73, No. 11, (Aug. 23, 2007), pp. 1190-1191.

* cited by examiner

*Primary Examiner* — Dennis Heyer
(74) *Attorney, Agent, or Firm* — Nixon & Vanderhye P.C.

(57) ABSTRACT

The present invention relates to novel composition for the treatment, co-treatment or prevention of inflammatory disorders comprising an effective amount of carnosic acid 12-methylether.

4 Claims, No Drawings

COMPOSITIONS

This application is the U.S. national phase of International Application No. PCT/EP2007/010076 filed 21 Nov. 2007, which designated the U.S. and claims priority to Europe Application No. 06024382.1 filed 24 Nov. 2006, the entire contents of each of which are hereby incorporated by reference.

The present invention relates to novel composition for the treatment, co-treatment or prevention of inflammatory disorders comprising an effective amount of carnosic acid 12-methylether Inflammatory disorders are one of the most important health problems in the world. Inflammation is in general a localized protective response of the body tissues to invasion of the host by foreign material or injurious stimuli. The causes of inflammation can be infectious agents such as bacteria, viruses, and parasites; or physical agents such as burns or radiation; or chemicals like toxins, drugs or industrial agents; or immunological reactions such as allergies and autoimmune responses or conditions associated with oxidative stress.

Inflammation is characterized by pain, redness, swelling, heat, and eventual loss of function of the affected area. These symptoms are the results of a complex series of interactions taking place between the cells of the immune system. The response of the cells results in an interacting network of several groups of inflammatory mediators: Proteins (e.g. cytokines, enzymes (e.g. proteases, peroxydase), major basic protein, adhesion molecules (ICAM, VCAM), lipid mediators (e.g. eicosanoids, prostaglandins, leukotrienes, platelet activating factor (PAF)), reactive oxygen species (e.g. hydroperoxides, superoxyde anion $O_2^-$, nitric oxide (NO) etc). However, many of those mediators of inflammation are also regulators of normal cellular activity. Thus, deficiencies of inflammatory reactions lead to a compromised host (i.e. infection) while uncontrolled and thus chronic inflammation leads to inflammatory diseases mediated in part by the excessive production of several of the above mentioned mediators.

Joint disorders are leading causes of disability and dysfunction in the elderly; almost 80% of people over age 60 show some evidence of these disorders. Age, genetic factors, muscle disuse and weakness, trauma, obesity and anatomical abnormalities contribute to the development of the disorder. Joint disorders can e.g. be caused by (chronic) inflammatory diseases of the joints as well as by cartilage degradation of one or several joints or a combination thereof. Cartilage degradation is defined within the framework of the invention as a metabolic disorder of joint cartilage characterized by increased production of cartilage-degrading enzymes such as matrix metalloproteases.

Acute and chronic inflammation resulting from an excessive biosynthesis of inflammatory mediators is involved in numerous inflammatory disorders such as arthritis (e.g. osteoarthritis, rheumatoid arthritis), asthma, inflammatory bowel diseases, inflammatory diseases of the skin (e.g. contact dermatitis [particularly diaper area dermatitis], atopic dermatitis, xerosis, eczema, rosacea, seborrhea, psoriasis, neurodermitis, acne, thermal and radiation burns such as sunburn, other types of skin inflammation, and the tissue-degenerating effects of aging and chronic inflammatory disorders, such as atherosclerosis, heart diseases, metabolic syndrome X, osteoporosis, cancer, Alzheimer's disease and pre-stages thereof such as mild cognitive impairment or photoageing which is a result of chronic skin inflammation.

Arthritis is a chronic (inflammatory) disease of the joints and encompasses many different forms. For example, arthritis includes rheumatoid arthritis, spondyloarthopathies, gouty arthritis, osteoarthritis, systemic lupus erythematosus and juvenile arthritis. Like asthma, rheumatoid arthritis is characterized at the molecular level by chronically unbalanced expression of cytokines, chemokines, kinins and their receptors, adhesion molecules and their respective receptors, as well as inflammatory enzymes.

Osteoarthritis is a joint disease caused by the breakdown and loss of the cartilage of one or more joints which develops by wear and tear of the joints during aging and results in pain and diminished joint function. Symptoms of osteoarthritis include pain, stiffness and loss of mobility in one or more joints. Excessive joint loading increases the risk of osteoarthritis, hence osteoarthritis mostly affects the weight-bearing joints such as spine, knees and hips, but thumb and finger joints may also be affected. Joint disorders can also results from injury, i.e. microdamage or blunt trauma, fractures, damage to tendons, menisci or ligaments or can be the result of excessive mechanical stress or other biomechanical instability resulting from for example an injury or obesity.

Psoriasis is one of the most common skin problems, affecting 1-3% of the human population. Inflammatory bowel disease is a general term used to describe gastrointestinal tract diseases and includes disorders such as ulcerative colitis and Crohn's disease.

Beside the process of intravascular lipid deposition, inflammatory reactions of the endothelial (i.e. blood vessel) wall are considered to critically contribute to atherosclerosis i.e. atheroma formation. Atherosclerosis results from vascular injury which triggers inflammation. Activated macrophages, T-lymphocytes, and eventually smooth muscle cells are present in atherosclerotic plaques. Monocyte/macrophage and lymphocyte activation leads to the release of eicosanoids, cytokines and matrix metalloproteinases (MMPs) which are implicated in endothelial damage, as well as in the formation and eventually the rupture of atherosclerotic plaques. Finally, circulating inflammatory markers such as C-reactive protein (CRP), fibrinogen, and interleukins are increased or altered in groups at high-risk of coronary artery diseases (CAD). Several clinical trials indicate that elevated CRP concentration correlates with increased risk of coronary, and vascular, events. Thus inflammation appears to play an important role in the initiation and progression of atheroma formation.

Inflammatory processes are also associated with the pathophysiology of Alzheimer's disease. There is evidence of inflammation in the brain of patients with Alzheimer's disease, as it is characterized by increased levels of cytokines and activated microglial cells. Thus, inflammation is not only involved in the classical inflammatory disorders (e.g., arthritis, asthma, bowel diseases) but is also associated with many chronic inflammatory disorders (e.g., atherosclerosis, heart diseases, metabolic syndrome X, osteoporosis, cancer, Alzheimer disease).

Inflammatory events are also associated with the pathophysiology of different types of cancers (e.g. gastric and intestinal cancers, melanomas). Increased levels of inflammatory mediators such as prostaglandins have been found in cancers of breast, colon, lung and pancreas in humans.

Currently, two main classes of drugs, the corticosteroid and the nonsteroidal anti-inflammatory drugs (NSAIDs) are used to treat inflammatory disorders and/or joint disorders. NSAIDs and corticosteroids provide essentially symptomatic relief. Use of corticosteroids has declined due to a growing concern about the serious side effects of prolonged use.

NSAIDs are among the most widely used drugs, primarily for the treatment of pain and inflammatory disorders, in particular for the treatment of arthritis (i.e. pain relief) but also for the treatment of cartilage degradation such as osteoarthritis. However, in the latter case, the drugs are given to control the pain and to restrain swelling, but do not prevent or treat damage to the cartilage.

Epidemiological studies have suggested that patients taking NSAIDs have a lower risk of developing Alzheimer's disease than those not taking NSAIDs. A protective effect of NSAIDs suggests that the cyclooxygenases might be involved in the neurodegenerative process.

Epidemiological studies showed a significant reduction in the risk of colorectal, gastric, esophageal, and breast cancers among people who take NSAIDs compared with those not taking NSAIDs. In animal models, NSAIDs significantly reduced tumor development.

However, long-term use of NSAIDs when treating chronic diseases such as arthritis or osteoarthritis is limited by severe side-effects like serious gastrointestinal complications, renal toxicity or asthmatic reactions.

For these reasons patients with inflammatory disorders have a special interest in a type of treatment considered as "natural" with mild anti-inflammatory effects and without major side effects, which can be used for disease prevention and as adjuvant treatment. Even though there are examples of "natural" agents with shown anti-inflammatory action these "natural" compounds often have an inadequate biological and thus inhibitory activity.

For the reasons outlined above, there is a great need for new anti-inflammatory agents and agents that treat joint disorders e.g. caused by cartilage degradation. Furthermore, there is a great need of agents that treat inflammatory skin conditions in order to maintain and/or achieve health and/or a beautiful appearance of the human skin.

Surprisingly it has been found that carnosic acid 12-methylether has an anti-inflammatory activity. Thus, carnsic acid 12-methylether is suitable to treat or prevent cartilage loss and damage and can consequently be used as an agent suitable for the treatment, co-treatment or prevention of inflammatory disorders and/or joint disorders. Furthermore, carnosic acid 12-methylether can be used to treat inflammatory skin conditions in order to maintain and/or achieve health and/or a beautiful appearance of the human skin Thus, the invention relates to a composition for the treatment, co-treatment or prevention of inflammatory disorders comprising an effective amount of carnosic acid 12-methylether. In a preferred embodiment the inflammatory disorder is a joint disorder, preferably arthritis, most preferably osteoarthritis and rheumatoid arthritis. In another preferred embodiment the inflammatory disorders are inflammatory skin conditions such as for example sunburn, photoageing, acne or impure skin.

The compositions according to the invention are preferably a nutraceutical, a pharmaceutical or a cosmetic or dermatological composition. Preferably, the nutraceutical is an oral composition, whereas the pharmaceutical or the cosmetic or dermatological composition may be an oral or a topical composition.

The term 'an effective amount' refers to an amount necessary to obtain a physiological effect. The physiological effect may be achieved by one single dose or by repeated doses. The effective amount of carnosic acid 12-methyl ether in a composition according to the invention may vary depending upon known factors, such as the physiological characteristics of the particular composition and its mode and route of administration; the age, health and weight of the recipient; the nature and extent of the symptoms; the kind of concurrent treatment; the frequency of treatment; and the effect desired which can be determined by the expert in the field with normal trials, or with the usual considerations regarding the formulation.

In another embodiment, the invention relates to the use of carnosic acid 12-methylether as given above for the manufacture of a nutraceutical or a pharmaceutical in particular for the manufacture of a nutraceutical or a pharmaceutical for the treatment, co-treatment or prevention of inflammatory disorders such as e.g. heart disease, multiple sclerosis, osteo- and rheumatoid arthritis, atherosclerosis, and osteoporosis, preferably of arthritis, in particular of osteoarthritis and rheumatoid arthritis as well as inflammatory skin conditions.

Also, carnosic acid 12-methylether is suitable for treatment, co-treatment and prevention of joint disorders in particular for reduction of joint inflammation, maintenance and/or improvement of joint health, prevention of joint stiffness, increase of joint mobility, providing supple and/or flexible joints, lubrication of the joints, relief of pain associated with joint inflammation, decrease of joint swelling, lessening joint problems, and providing joint care. Thus, the invention also relates to the use of carnosic acid 12-methylether for the manufacture of a nutraceutical or pharmaceutical for the treatment, co-treatment or prevention of joint disorders.

Further objects of the present invention are the use of carnosic acid 12-methylether as cartilage-regenerating and -maintaining agent as well as the use of carnosic acid 12-methylether as given above (for the manufacture of a composition) for the maintenance and regeneration of articular cartilage.

In all embodiments of the invention the term carnosic acid 12-methylether also encompasses any material or extract of a plant containing carnosic acid 12-methylether in an amount of at least 30 weight-% (i.e. from 30 to 100 weight-%), preferably in an amount of at least 50 weight-% (i.e. from 50 to 100 weight-%), more preferably in an amount of at least 70 weight-% (i.e. from 70 to 100 weight-%), most preferably in an amount of at least 90 weight-% (i.e. from 90 to 100 weight-%), based on the total weight of the plant material or extract. The terms "material of a plant" and "plant material" used in the context of the present invention mean any part of a plant.

"Carnosic acid 12-methyl ether" means the racemic mixture as well as pure (4aR,10aS)-carnosic acid 12-methyl ether or pure (4aS,10aR)-carnosic acid 12-methyl ether or any mixture or diastereoisomer of them. Carnosic acid 12-methyl ether can be isolated from plants like sage, rosemary, *Hyptis martiusii*, but not limited to it. Therefore, any material or extract of these plants or any other plant material or extract containing carnosic acid 12-methyl ether in an amount of at least 30 weight-% (i.e. from 30 to 100 weight-%), preferably in an amount of at least 50 weight-% (i.e. from 50 to 100 weight-%), more preferably in an amount of at least 70 weight-% (i.e. from 70 to 100 weight-%), most preferably in an amount of at least 90 weight-% (i.e. from 90 to 100 weight-%), based on the total weight of the plant material or extract, is also encompassed by this expression. "Carnosic acid 12-methyl ether" means both "natural" (isolated) and "synthetic" (manufactured) carnosic acid 12-methyl ether.

The structure of (4aR,10aS)-carnosic acid 12-methyl ether (CAS 62201-71-2) is depicted below Formula I

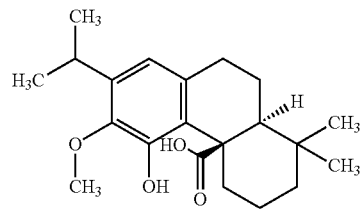

(4aR,10aS)-carnosic acid 12-methyl ether (CAS 62201-71-2)

Beside the (pure) compound carnosic acid 12-methyl ether especially preferred are plant materials and plant extracts containing at least 30 weight-% (i.e. from 30 to 100 weight-%), preferably at least 50 weight-% (i.e. from 50 to 100 weight-%), more preferably at least 70 weight-% (i.e. from 70 to 100 weight-%), most preferably at least 90 weight-% (i.e. from 90 to 100 weight-%) of carnosic acid 12-methyl ether, based on the total weight of the plant material/extract.

In the context of this invention "treatment" also encompasses co-treatment as well as prevention. "Prevention" can be the prevention of the first occurrence (primary prevention) or the prevention of a reoccurrence (secondary prevention). In the context of this invention the term "disorder" also encompasses diseases.

The dosage and ratios of the at carnosic acid 12-methyl ether to an animal including humans may vary depending upon known factors, such as the physiological characteristics of the particular composition and its mode and route of administration; the age, health and weight of the recipient; the nature and extent of the symptoms; the kind of concurrent treatment; the frequency of treatment; and the effect desired which can be determined by the expert in the field with normal trials, or with the usual considerations regarding the formulation. A suitable daily dosage of carnosic acid 12-methyl ether for oral intake by humans may be within the range of from 0.001 mg per kg body weight to about 40 mg per kg body weight per day. More preferred is a daily dosage of from about 0.01 to about 10 mg per kg body weight, and especially preferred is a daily dosage of from about 0.05 to 5.0 mg per kg body weight. The amount of a plant material or plant extract containing carnosic acid 12-methyl ether can be calculated accordingly. In solid dosage unit preparations for humans, the carnosic acid 12-methyl ether is suitably present in an amount in the range of from about 0.1 mg to about 1000 mg, preferably in the range of from about 1 mg to about 500 mg per dosage unit.

In a different aspect, the invention also relates to carnosic acid 12-methyl ether for use as a medicament/composition for the treatment, co-treatment or prevention of inflammatory disorders such as arthritis, in particular of osteoarthritis and rheumatoid arthritis and/or for the treatment, co-treatment or prevention of joint disorders and/or for the treatment, co-treatment or prevention of inflammatory skin conditions.

In another aspect, the invention relates to a nutraceutical comprising carnosic acid 12-methyl ether and a nutraceutically acceptable carrier. In one preferred embodiment, the invention relates to a nutraceutical comprising carnosic acid 12-methyl ether and a nutraceutically acceptable carrier for the treatment, co-treatment or prevention of inflammatory disorders such as arthritis, in particular of osteoarthritis and rheumatoid arthritis and/or joint disorders. In another preferred embodiment the invention relates to a nutraceutical comprising carnosic acid 12-methyl ether and a nutraceutically acceptable carrier for the treatment, co-treatment or prevention of inflammatory skin conditions.

Also, the invention relates to a method for treatment, co-treatment and prevention of inflammatory disorders such as for example arthritis, in particular of osteoarthritis and rheumatoid arthritis and/or joint disorders in animals including humans said method comprising the step of administering an effective amount of carnosic acid 12-methyl ether to animals including humans, which are in need thereof.

Furthermore the invention relates to a method for the regeneration and/or maintenance of (articular) cartilage in a mammal which comprises administering to a mammal in need of such regeneration and/or maintenance an effective amount of carnosic acid 12-methylether.

The term 'an effective amount' refers to an amount necessary to obtain a physiological effect. The physiological effect may be achieved by one single dose or by repeated doses. The dosage administered may, of course, vary depending upon known factors, such as the physiological characteristics of the particular composition and its mode and route of administration; the age, health and weight of the recipient; the nature and extent of the symptoms; the kind of concurrent treatment; the frequency of treatment; and the effect desired and can be adjusted by a person skilled in the art.

In the framework of the invention, with animals is meant all animals, including mammals, examples of which include humans. Preferred examples of mammals beside humans are non-ruminant or ruminant animals, pet animals and birds including cats, dogs, cattle, swine, turkeys, dromedaries, camels, elephants, and horses.

The term nutraceutical as used herein include food product, foodstuff, dietary supplement, nutritional supplement or a supplement composition for a food product or a foodstuff.

In another embodiment the present invention relates to a nutraceutical comprising carnosic acid 12-methylether in particular for the treatment, co-treatment or prevention of inflammatory disorders such as arthritis, in particular of osteoarthritis and rheumatoid arthritis and/or joint disorders and/or inflammatory conditions of the skin wherein the nutraceutical is a food product, foodstuff, dietary supplement, nutritional supplement or a supplement composition for a food product or a foodstuff preferably a dietary supplement, a nutritional supplement or a supplement composition for a food or a foodstuff.

As used herein, the term food product refers to any food or feed suitable for consumption by humans or animals. The food product may be a prepared and packaged food (e.g., mayonnaise, salad dressing, bread, or cheese food) or an animal feed (e.g., extruded and pelleted animal feed, coarse mixed feed or pet food composition). As used herein, the term foodstuff refers to any substance fit for human or animal consumption. The term dietary supplement refers to a small amount of a compound for supplementation of a human or animal diet packaged in single or multiple dose units. Dietary supplements do not generally provide significant amounts of calories but may contain other micronutrients (e.g., vitamins or minerals). The term nutritional supplement refers to a composition comprising a dietary supplement in combination with a source of calories. In some embodiments, nutritional supplements are meal replacements or supplements (e.g., nutrient or energy bars or nutrient beverages or concentrates).

Food products or foodstuffs are for example beverages such as non-alcoholic and alcoholic drinks as well as liquid preparation to be added to drinking water and liquid food, non-alcoholic drinks are for instance soft drinks, sport drinks, fruit juices, such as for example orange juice, apple juice and grapefruit juice; lemonades, teas, near-water drinks and milk and other dairy drinks such as for example yoghurt drinks, and diet drinks. In another embodiment food products or foodstuffs refer to solid or semi-solid foods comprising the composition according to the invention. These forms can include, but are not limited to baked goods such as cakes and cookies, puddings, dairy products, confections, snack foods, or frozen confections or novelties (e.g., ice cream, milk shakes), prepared frozen meals, candy, snack products (e.g., chips), liquid food such as soups, spreads, sauces, salad dressings, prepared meat products, cheese, yogurt and any other fat or oil containing foods, and food ingredients (e.g., wheat flour).

The term food products or foodstuffs also includes functional foods and prepared food products, the latter referring to any pre-packaged food approved for human consumption.

Animal feed including pet food compositions advantageously include food intended to supply necessary dietary requirements, as well as treats (e.g., dog biscuits) or other food supplements. The animal feed comprising the composition according to the invention may be in the form of a dry composition (for example, kibble), semi-moist composition, wet composition, or any mixture thereof. Alternatively or additionally, the animal feed is a supplement, such as a gravy, drinking water, yogurt, powder, suspension, chew, treat (e.g., biscuits) or any other delivery form. Dietary supplements of the present invention may be delivered in any suitable format. In preferred embodiments, dietary supplements are formulated for oral delivery. The ingredients of the dietary supplement of this invention are contained in acceptable excipients and/or carriers for oral consumption. The actual form of the carrier, and thus, the dietary supplement itself, is not critical. The carrier may be a liquid, gel, gelcap, capsule, powder, solid tablet (coated or non-coated), tea, or the like. The dietary supplement is preferably in the form of a tablet or capsule and most preferably in the form of a hard (shell) gelatin capsule. Suitable excipient and/or carriers include maltodextrin, calcium carbonate, dicalcium phosphate, tricalcium phosphate, microcrystalline cellulose, dextrose, rice flour, magnesium stearate, stearic acid, croscarmellose sodium, sodium starch glycolate, crospovidone, sucrose, vegetable gums, lactose, methylcellulose, povidone, carboxymethylcellulose, corn starch, and the like (including mixtures thereof). Preferred carriers include calcium carbonate, magnesium stearate, maltodextrin, and mixtures thereof. The various ingredients and the excipient and/or carrier are mixed and formed into the desired form using conventional techniques. The tablet or capsule of the present invention may be coated with an enteric coating that dissolves at a pH of about 6.0 to 7.0. A suitable enteric coating that dissolves in the small intestine but not in the stomach is cellulose acetate phthalate. Further details on techniques for formulation for and administration may be found in the latest edition of Remington's Pharmaceutical Sciences (Maack Publishing Co., Easton, Pa.).

In other embodiments, the dietary supplement is provided as a powder or liquid suitable for adding by the consumer to a food or beverage. For example, in some embodiments, the dietary supplement can be administered to an individual in the form of a powder, for instance to be used by mixing into a beverage, or by stirring into a semi-solid food such as a pudding, topping, sauce, puree, cooked cereal, or salad dressing, for instance, or by otherwise adding to a food e.g. enclosed in caps of food or beverage container for release immediately before consumption. The dietary supplement may comprise one or more inert ingredients, especially if it is desirable to limit the number of calories added to the diet by the dietary supplement. For example, the dietary supplement of the present invention may also contain optional ingredients including, for example, herbs, vitamins, minerals, enhancers, colorants, sweeteners, flavorants, inert ingredients, and the like.

In some embodiments, the dietary supplements further comprise vitamins and minerals including, but not limited to, calcium phosphate or acetate, tribasic; potassium phosphate, dibasic; magnesium sulfate or oxide; salt (sodium chloride); potassium chloride or acetate; ascorbic acid; ferric orthophosphate; niacinamide; zinc sulfate or oxide; calcium pantothenate; copper gluconate; riboflavin; beta-carotene; pyridoxine hydrochloride; thiamin mononitrate; folic acid; biotin; chromium chloride or picolonate; potassium iodide; sodium selenate; sodium molybdate; phylloquinone; vitamin D3; cyanocobalamin; sodium selenite; copper sulfate; vitamin A; vitamin C; inositol; potassium iodide. Suitable dosages for vitamins and minerals may be obtained, for example, by consulting the U.S. RDA guidelines.

In other embodiments, the present invention provides nutritional supplements (e.g., energy bars or meal replacement bars or beverages) comprising the composition according to the invention. The nutritional supplement may serve as meal or snack replacement and generally provides nutrient calories. Preferably, the nutritional supplements provide carbohydrates, proteins, and fats in balanced amounts. The nutritional supplement can further comprise carbohydrate, simple, medium chain length, or polysaccharides, or a combination thereof. A simple sugar can be chosen for desirable organoleptic properties. Uncooked cornstarch is one example of a complex carbohydrate. If it is desired that it should maintain its high molecular weight structure, it should be included only in food formulations or portions thereof which are not cooked or heat processed since the heat will break down the complex carbohydrate into simple carbohydrates, wherein simple carbohydrates are mono- or disaccharides. The nutritional supplement contains, in one embodiment, combinations of sources of carbohydrate of three levels of chain length (simple, medium and complex; e.g., sucrose, maltodextrins, and uncooked cornstarch).

Sources of protein to be incorporated into the nutritional supplement of the invention can be any suitable protein utilized in nutritional formulations and can include whey protein, whey protein concentrate, whey powder, egg, soy flour, soy milk, soy protein, soy protein isolate, caseinate (e.g., sodium caseinate, sodium calcium caseinate, calcium caseinate, potassium caseinate), animal and vegetable protein and hydrolysates or mixtures thereof. When choosing a protein source, the biological value of the protein should be considered first, with the highest biological values being found in caseinate, whey, lactalbumin, egg albumin and whole egg proteins. In a preferred embodiment, the protein is a combination of whey protein concentrate and calcium caseinate. These proteins have high biological value; that is, they have a high proportion of the essential amino acids. See Modern Nutrition in Health and Disease, eighth edition, Lea & Febiger, publishers, 1986, especially Volume 1, pages 30-32. The nutritional supplement can also contain other ingredients, such as one or a combination of other vitamins, minerals, antioxidants, fiber and other dietary supplements (e.g., protein, amino acids, choline, lecithin, omega-3 fatty acids). Selection of one or several of these ingredients is a matter of formulation, design, consumer preference and end-user. The amounts of these ingredients added to the dietary supplements of this invention are readily known to the skilled artisan. Guidance to such amounts can be provided by the U.S. RDA doses for children and adults. Further vitamins and minerals that can be added include, but are not limited to, calcium phosphate or acetate, tribasic; potassium phosphate, dibasic; magnesium sulfate or oxide; salt (sodium chloride); potassium chloride or acetate; ascorbic acid; ferric orthophosphate; niacinamide; zinc sulfate or oxide; calcium pantothenate; copper gluconate; riboflavin; beta-carotene; pyridoxine hydrochloride; thiamin mononitrate; folic acid; biotin; chromium chloride or picolonate; potassium iodide; sodium selenate; sodium molybdate; phylloquinone; vitamin D3; cyanocobalamin; sodium selenite; copper sulfate; vitamin A; vitamin C; inositol; potassium iodide.

The nutritional supplement can be provided in a variety of forms, and by a variety of production methods. In a preferred embodiment, to manufacture a food bar, the liquid ingredients are cooked; the dry ingredients are added with the liquid ingredients in a mixer and mixed until the dough phase is reached; the dough is put into an extruder, and extruded; the extruded dough is cut into appropriate lengths; and the product is cooled. The bars may contain other nutrients and fillers to enhance taste, in addition to the ingredients specifically listed herein.

It is understood by those of skill in the art that other ingredients can be added to those described herein, for example, fillers, emulsifiers, preservatives, etc. for the processing or manufacture of a nutritional supplement.

Additionally, flavors, coloring agents, spices, nuts and the like may be incorporated into the nutraceutical composition. Flavorings can be in the form of flavored extracts, volatile oils, chocolate flavorings, peanut butter flavoring, cookie crumbs, crisp rice, vanilla or any commercially available flavoring. Examples of useful flavoring include, but are not limited to, pure anise extract, imitation banana extract, imitation cherry extract, chocolate extract, pure lemon extract, pure orange extract, pure peppermint extract, imitation pineapple extract, imitation rum extract, imitation strawberry extract, or pure vanilla extract; or volatile oils, such as balm oil, bay oil, bergamot oil, cedarwood oil, walnut oil, cherry oil, cinnamon oil, clove oil, or peppermint oil; peanut butter, chocolate flavoring, vanilla cookie crumb, butterscotch or toffee. In one embodiment, the dietary supplement contains cocoa or chocolate.

Emulsifiers may be added for stability of the nutraceutical. Examples of suitable emulsifiers include, but are not limited to, lecithin (e.g., from egg or soy), and/or mono- and di-glycerides. Other emulsifiers are readily apparent to the skilled artisan and selection of suitable emulsifier(s) will depend, in part, upon the formulation and final product. Preservatives may also be added to the nutritional supplement to extend product shelf life. Preferably, preservatives such as potassium sorbate, sodium sorbate, potassium benzoate, sodium benzoate or calcium disodium EDTA are used.

In addition to the carbohydrates described above, the nutraceutical can contain natural or artificial (preferably low calorie) sweeteners, e.g., saccharides, cyclamates, aspartamine, aspartame, acesulfame K, and/or sorbitol. Such artificial sweeteners can be desirable if the nutritional supplement is intended to be consumed by an overweight or obese individual, or an individual with type II diabetes who is prone to hyperglycemia.

Moreover, a multi-vitamin and mineral supplement may be added to the nutraceuticals of the present invention to obtain an adequate amount of an essential nutrient, which is missing in some diets. The multi-vitamin and mineral supplement may also be useful for disease prevention and protection against nutritional losses and deficiencies due to lifestyle patterns. The dosage and ratios of carnosic acid 12-methyl ether administered via a nutraceutical will, of course, vary depending upon known factors, such as the physiological characteristics of the particular composition and its mode and route of administration; the age, health and weight of the recipient; the nature and extent of the symptoms; the kind of concurrent treatment; the frequency of treatment; and the effect desired which can be determined by the expert in the field with normal trials, or with the usual considerations regarding the formulation of a nutraceutical.

A nutraceutical according to the invention may comprise carnosic acid 12-methyl ether in an amount of about 0.001 mg to 1 g, preferably in an amount from 0.01 mg to 1 g, most preferably in the range of 2.0 mg to 300 mg per serving.

In dietary compositions, especially in food and beverages for humans the carnosic acid 12-methyl ether is suitably present in an amount in the range of from about 0.0001 (1 mg/kg) to about 5 weight-% (50 g/kg), preferably from about 0.001% (10 mg/kg) to about 1 weight-%, (10 g/kg) more preferably from about 0.01 (100 mg/kg) to about 0.5 weight-% (5 g/kg), based upon the total weight of the food or beverage.

In food and drinks in a preferred embodiment of the invention the amount of carnosic acid 12-methyl ether is in the range of from 10 to 30 mg per serving, i.e. 120 mg per kg food or drink.

For animals excluding humans a suitable daily dosage of carnosic acid 12-methyl ether, for the purposes of the present invention may be within the range of from 0.001 mg per kg body weight to about 1000 mg per kg body weight per day. More preferred is a daily dosage in the range of from about 0.1 mg to about 500 mg per kg body weight, and especially preferred is a daily dosage in the range of from about 1 mg to 100 mg per kg body weight.

If instead of the pure compounds a plant material or plant extract comprising carnosic acid 12-methyl ether the dosages to be applied can be calculated accordingly.

In another aspect, the invention relates to a pharmaceutical comprising carnosic acid 12-methyl ether and a pharmaceutically acceptable. In a preferred embodiment the invention relates to a pharmaceutical comprising carnosic acid 12-methyl ether and a pharmaceutically acceptable carrier for the treatment, co-treatment or prevention of inflammatory disorders such as arthritis, in particular of osteoarthritis and rheumatoid arthritis and/or joint disorders. In another preferred embodiment the invention relates to a pharmaceutical comprising carnosic acid 12-methyl ether and a pharmaceutically acceptable carrier for the treatment, co-treatment or prevention of inflammatory skin conditions.

A person skilled in the art knows which carriers can be used as pharmaceutically acceptable carriers. Suitable pharmaceutical carriers are e.g. described in Remington's Pharmaceutical Sciences, supra, a standard reference text in this field. Examples of such pharmaceutically acceptable carriers are both inorganic and organic carrier materials, suitable for oral/parenteral/injectable administration and include water, gelatin, gum arabic, lactose, starch, magnesium stearate, talc, vegetable oils, and the like.

The pharmaceutical may further comprise conventional pharmaceutical additives and adjuvants, excipients or diluents, including, but not limited to, water, gelatin of any origin, vegetable gums, ligninsulfonate, talc, sugars, starch, gum arabic, vegetable oils, polyalkylene glycols, flavoring agents, preservatives, stabilizers, emulsifying agents, buffers, lubricants, colorants, wetting agents, fillers, and the like.

In a preferred embodiment the pharmaceutical is in the form of a powder, tablet, capsule, gel, liquid or solid embodiment.

The dosages and ratios of the individual components in a pharmaceutical can be determined by the expert in the field with normal preclinical and clinical trials, or with the usual considerations regarding the formulation of pharmaceutical composition.

The pharmaceutical may comprise carnosic acid 12-methyl ether in an amount from preferably 1 mg to 2000 mg per dosage unit, e.g., per capsule or tablet, or from 1 mg per daily dose to 3000 mg per daily dose of a liquid formulation. In a preferred embodiment carnosic acid 12-methyl ether, preferably in the form an enriched plant extract encompassing carnosic acid 12-methyl ether in an amount of at least 30 weight-% is administered via a pharmaceutical composition either in the form of a single dose or by multiple doses in an amount of at least 0.01 mg/kg bodyweight/day, preferably in an amount of 0.1-50 mg/kg body weight/day, most preferably in an amount of 0.3-15 mg/kg body weight/day. If instead of the pure compounds a plant material or plant extract comprising carnosic acid 12-methyl ether the dosages to be applied can be calculated accordingly.

The nutraceuticals and pharmaceuticals according to the present invention may be in any galenic form that is suitable for administering to the animal body including the human body, more in particular in any form that is conventional for oral administration, e.g. in solid form, for example as (additives/supplements for) food or feed, food or feed premixes, fortified food or feed, tablets, pills, granules, dragées, capsules, and effervescent formulations such as powders and tablets, or in liquid form, for instance in the form of solutions, emulsions or suspensions, for example as beverages, pastes and oily suspensions. The pastes may be filled into hard or soft shell capsules. Examples for other application forms are forms for transdermal, parenteral, topical or injectable administration. The nutraceutical and pharmaceutical compositions may be in the form of controlled (delayed) release formulations. Examples of pharmaceutical compositions also include compositions suitable for topical application and transdermal absorption of the phenolic compound, such as crèmes, gels, sprays, dry sticks, powders etc.

Moreover, a multi-vitamin and mineral supplement may be added to the nutraceuticals or pharmaceuticals of the present invention to obtain an adequate amount of an essential nutrient, which is missing in some diets. The multi-vitamin and mineral supplement may also be useful for disease prevention and protection against nutritional losses and deficiencies due to lifestyle patterns.

A person skilled in the art knows which carriers can be used as pharmaceutically acceptable carriers. Examples of such pharmaceutically acceptable carriers are both inorganic and organic carrier materials, suitable for oral/parenteral/injectable administration and include water, gelatin, gum arabic, lactose, starch, magnesium stearate, talc, vegetable oils, and the like.

Besides carnosic acid 12-methyl ether and a pharmaceutically acceptable carrier, the pharmaceutical composition according to the present invention, may further comprise conventional pharmaceutical additives and adjuvants, excipients or diluents, including, but not limited to, water, gelatin of any origin, vegetable gums, ligninsulfonate, talc, sugars, starch, gum Arabic, vegetable oils, polyalkylene glycols, flavoring agents, preservatives, stabilizers, emulsifying agents, buffers, lubricants, colorants, wetting agents, fillers, and the like.

The carnosic acid 12-methyl ether may be used in combination with other nutraceutical compositions or therapeutic agents known to those skilled in the art for treatment or prevention of inflammatory disorder and/or joint disorders and/or inflammatory skin conditions by administration prior to, simultaneously with or following the administration of carnosic acid 12-methyl ether.

According to the present invention not only carnosic acid 12-methyl ether but also plant materials and extracts containing them in an amount of at least 30 weight-% (i.e. from 30 to 100 weight-%), preferably in an amount of at least 50 weight-% (i.e. from 50 to 100 weight-%), more preferably in an amount of at least 70 weight-% (i.e. from 70 to 100 weight-%), most preferably in an amount of at least 90 weight-% (i.e. from 90 to 100 weight-%), based on the total weight of the plant material or extract, as well as dietary and pharmaceutical compositions containing them can be used as medicament, especially for the treatment, co-treatment or prevention of inflammatory disorders such as for example arthritis, in particular of osteoarthritis and rheumatoid arthritis and/or for the treatment, co-treatment or prevention of joint disorders and/or for the treatment, co-treatment or prevention inflammatory skin conditions.

The carnosic acid 12-methyl ether as well as (mixtures of) plant materials and plant extracts containing them (especially in an amount of at least 30 weight-%, preferably in an amount of at least 50 weight-%, more preferably in an amount of from 70 to 90 weight-%, most preferably in an amount of at least 90 weight-%, based on the total weight of the plant material or extract), and dietary/pharmaceutical compositions containing them are thus suitable for the treatment of animals including humans.

In yet another aspect the invention also relates to a composition comprising carnosic acid 12-methylether for the treatment, co-treatment or prevention of inflammatory skin conditions. The composition comprising carnosic acid 12-methylether for the treatment, co-treatment or prevention of inflammatory skin conditions may be designed for oral administration such as e.g. a nutraceutical or a pharmaceutical or a medicament or may be designed for topical application such as a cream or lotion without being limited hereto. If the composition comprising carnosic acid 12-methylether for the treatment, co-treatment or prevention of inflammatory conditions of the skin is intended for oral administration it may be in the form of a nutraceutical or a pharmaceutical with all the definitions and preferences as given above. Such products are also known as beauty foods and supplements.

The term 'inflammatory skin conditions' encompasses inflammatory diseases of the skin such as e.g. contact dermatitis [particularly diaper area dermatitis], atopic dermatitis, xerosis, eczema, rosacea, seborrhea, psoriasis, neurodermitis, acne, thermal and radiation burns such as sunburn as well as any other types of skin inflammation such as e.g. photoageing which is a result of chronic skin inflammation. The term 'inflammatory skin conditions' also encompasses the term 'Impure skin'. "Impure skin' can be caused by various factors: skin irritation through various exogenous and endogenous stimuli (e.g. sun, wind, cold, dryness, incompatibility or sensitivity to crèmes, or other skin care products, overproduction of sebum consequently leading to pimples, black spots and acne). It is generally accepted that inflammatory processes in the epidermis are involved in the processes leading to skin irritation, sensitive skin and impure skin. It is furthermore well established, that in these mechanisms cytokines play an important role. Pro-inflammatory cytokines are released from keratinocytes in the epidermis upon inflammatory stimuli (Boniface K, Lecron J C, Bernard F X, Dagregorio G, Guillet G, Nau F, Morel F. Keratinocytes as targets for interleukin-10-related cytokines: a putative role in the pathogenesis of psoriasis, Eur. Cytokine Netw. 2005 December; 16(4):309-19).

Accordingly, reduction of the response of skin cells to inflammatory stimuli can lead to an improvement of an impure or sensitive skin condition and may help to produce a pure skin with healthy and natural radiance and glow.

Thus, the invention also relates to the use of a composition according to the invention for promoting an optimal health, natural radiance and glow and/or a beautiful look of the skin. Furthermore, the invention encompasses the use of a composition according to the invention for supporting a clear, pure appearance of the skin.

In yet another aspect the invention also relates to the use of carnosic acid 12-methylether for the treatment, co-treatment or prevention of inflammatory skin conditions such as sunburn, impure skin such as acne or the results of chronic skin inflammation such as photoageing.

In another aspect, the invention relates to a cosmetic or dermatological preparation (the latter preparation are a specific type of a pharmaceutical) comprising an effective amount of carnosic acid 12-methylether or compositions containing them (plant materials/extracts containing them in an amount of at least 30 weight-%, preferably in an amount of at least 50 weight-%, more preferably in an amount of from 70 to 90 weight-%, most preferably in an amount of at least 90 weight-%, based on the total weight of the plant material or extract; dietary/pharmaceutical compositions) and a cosmetically or dermatologically acceptable carrier.

The cosmetic or dermatological composition may further comprise conventional cosmetic respectively dermatological adjuvants and/or additives and/or additional active ingredients.

Preferably the cosmetic or dermatological preparations are skin care formulations for the treatment, co-treatment or prevention of inflammatory skin conditions, in particular of sunburn caused by UV-radiation, of contact dermatitis (particularly diaper area dermatitis), atopic dermatitis, xerosis, eczema, rosacea, seborrhea, psoriasis, neurodermitis, thermal burns, photoageing or for the treatment, co-treatment or prevention of impure skin such as acne as well as of sensitive skin towards environmental stressors (wind, soaps, dry climate). Examples of impure skin include pimples, acne and other skin impurities with an inflammatory aspect.

The term "effective amount" means preferably at least 0.001% of each active agents based on the total weight of the cosmetic or dermatological composition. Preferably, the cosmetic or dermatological preparations comprise the carnosic acid 12-methylether in an amount between 0.01 wt.-% and 20 wt.-%, more preferably between 0.05 and 10 wt.-%, still more preferably between 0.1 and 5 wt.-%.

The amount of the cosmetic or dermatological preparation which is to be applied to the skin depends on the concentration of the active ingredients in the preparation and the desired cosmetic or pharmaceutical effect. For example, the application can be such that a crème is applied to the skin. A crème is usually applied in an amount of about 1 to 2 mg crème/cm$^2$ skin. The amount of the composition which is applied to the skin is, however, not critical, and if with a certain amount of applied composition the desired effect cannot be achieved, a higher concentration of the active preparations which contain more active ingredient might be employed.

The invention also relates to the use of the cosmetic preparation for the cosmetic treatment, co-treatment or prevention of inflammatory skin conditions, in particular for the cosmetic treatment, co-treatment or prevention of sunburn, contact dermatitis (particularly diaper area dermatitis), atopic dermatitis, xerosis, eczema, rosacea, seborrhea, psoriasis, neurodermitis, acne, thermal burns or photoageing, and sensitive skin towards environmental stressors (such as wind, soaps, dry climate).

Also, the invention relates to a method for the treatment, co-treatment or prevention of inflammatory skin conditions, in particular of sunburn in humans, of impure skin such as for example acne or of photoageing which is associated with chronic skin inflammation, said method comprising the step of administering an effective amount of the dermatological composition according to the invention to humans, which are in need thereof. Also, the invention relates to a method for cosmetic treatment, co-treatment or prevention of inflammatory skin conditions, in particular of sunburn or of impure skin such as acne by a cosmetic preparation according to the invention. Sunburn prevention is preferably achieved with topical application comprising the composition of the invention preferably in combination with suitable light screening agents.

The cosmetic or dermatological preparations according to the invention may be in the form of a suspension or dispersion in solvents or fatty substances, or alternatively in the form of an emulsion or micro emulsion (in particular of O/W or W/O type, O/W/0 or W/O/W-type, wherein 0 stands for oil phase and wherein W stands for water phase), such as a cream, a paste, a lotion, a thickened lotion or a milk, a vesicular dispersion in the form of an ointment, a gel, a solid tube stick or an aerosol mousse, and may be provided in the form of a mousse, foam or a spray foams, sprays, sticks or aerosols or wipes. Examples of cosmetic or dermatological preparations are skin care preparations, in particular, body oils, body lotions, body gels, treatment creams, skin protection ointments, moisturizing gels, moisturizing sprays, revitalizing body sprays, after sun preparations or sunscreen formulations.

The cosmetic or dermatological composition for the treatment, co-treatment or prevention of inflammatory skin conditions, such as for example sunburn, photoageing or impure skin may be in a form that is conventional for oral administration, examples of which are described above and also include beauty foods and supplements.

The cosmetic or dermatological preparations of the invention for instance as sunscreen formulations or after sun preparations may further comprise the usual cosmetic respectively dermatological adjuvants and/or additives such as preservatives/antioxidants, fatty substances/oils, water, organic solvents, silicones, thickeners, softeners, emulsifiers, additional light screening agents, antifoaming agents, moisturizers, fragrances, surfactants, fillers, sequestering agents, anionic, cationic, nonionic or amphoteric polymers or mixtures thereof, propellants, acidifying or basifying agents, dyes, colorants, pigments or nanopigments, light stabilizers, insect repellants, skin tanning agents, skin whitening agents, antibacterial agents, preservatives active ingredients or any other ingredients usually formulated into cosmetics.

Light screening agents which may be incorporated into cosmetic or dermatological preparations of the invention for instance sunscreen formulations are advantageously selected from IR, UV-A, UV-B, UV-C and/or broadband filters. Examples of UV-B or broad spectrum screening agents, i.e. substances having absorption maxima between about 290 and 340 nm may be organic or inorganic compounds. Organic UV-B or broadband screening agents are e.g. acrylates such as 2-ethylhexyl 2-cyano-3,3-diphenylacrylate (octocrylene, PARSOL® 340), ethyl 2-cyano-3,3-diphenylacrylate and the like; camphor derivatives such as 4-methyl benzylidene camphor (PARSOL® 5000), 3-benzylidene camphor, camphor benzalkonium methosulfate, polyacrylamidomethyl benzylidene camphor, sulfo benzylidene camphor, sulphomethyl benzylidene camphor, therephthalidene dicamphor sulfonic acid and the like; Cinnamate derivatives such as ethylhexyl methoxycinnamate (PARSOL® MCX), ethoxyethyl methoxycinnamate, diethanolamine methoxycinnamate (PARSOL® Hydro), isoamyl methoxycinnamate and the like as well as cinnamic acid derivatives bond to siloxanes; p-aminobenzoic acid derivatives, such as p-aminobenzoic acid, 2-ethylhexyl p-dimethylaminobenzoate, N-oxypropylenated ethyl p-aminobenzoate, glyceryl p-aminobenzoate; benzophenones such as benzophenone-3, benzophenone-4,2,2', 4,4'-tetrahydroxy-benzophenone, 2,2'-dihydroxy-4,4'-dimethoxybenzophenone and the like; esters of benzalmalonic acid such as di-(2-ethylhexyl) 4-methoxybenzalmalonate; esters of 2-(4-ethoxy-anilinomethylene)propandioic acid such as 2-(4-ethoxy anilinomethylene) propandioic acid diethyl ester as described in the European Patent Publication EP 0895 776; organosiloxane compounds containing benzmalonate groups as described in the European Patent Publications EP 0358584 B1, EP 0538431 B1 and EP 0709080 A1 such as polysilicone-15 (PARSOL® SLX); drometrizole trisiloxane (Mexoryl XL); imidazole derivatives such as e.g. 2-phenyl benzimidazole sulfonic acid and its salts (PARSOL®HS). Salts of 2-phenyl benzimidazole sulfonic acid are e.g. alkali salts such as sodium- or potassium salts, ammonium salts, morpholine salts, salts of primary, sec. and tert. amines like monoethanol amine salts, diethanol amine salts and the like; salicylate derivatives such as isopropylbenzyl salicylate, benzyl salicylate, butyl salicylate, ethylhexyl salicylate (PARSOL® EHS, NEO Heliopan OS), isooctyl salicylate or homomethyl salicylate (homosalate, PARSOL® HMS, NEO Heliopan OS) and the like; triazine derivatives such as ethylhexyl triazone (Uvinul T-150), diethylhexyl butamido triazone (Uvasorb HEB). Encapsulated UV-filters such as encapsulated ethylhexyl methoxycinnamate (Eusolex UV-pearls) or microcapsules loaded with UV-filters as e.g. disclosed in EP 1471995 and the like. Inorganic compounds are pigments such as microparticulated $TiO_2$, ZnO and the like. The term "microparticulated" refers to a particle size from about 5 nm to about 200 nm, particularly from about 15 nm to about 100 nm. The $TiO_2$ particles may also be coated by metal oxides such as e.g. aluminum or zirconium oxides or by organic coatings such as e.g. polyols, methicone, aluminum stearate, alkyl silane. Such coatings are well known in the art.

Examples of broad spectrum or UV A screening agents i.e. substances having absorption maxima between about 320 and 400 nm may be organic or inorganic compounds e.g. dibenzoylmethane derivatives such as 4-tert. butyl-4'-methoxy-dibenzoyl-methane (PARSOL® 1789), dimethoxydibenzoylmethane, isopropyldibenzoylmethane and the like; benzotriazole derivatives such as 2,2'-methylene-bis-(6-(2H-benzotriazole-2-yl)-4-(1,1,3,3,-tetramethylbutyl)-phenol (TINOSORB M) and the like; bis-ethylhexyloxyphenol methoxyphenyl triazine (Tinosorb S) and the like; phenylene-1,4-bis-benzimidazolsulfonic acids or salts such as 2,2-(1,4-phenylene)bis-(1H-benzimidazol-4,6-disulfonic acid) (Neoheliopan AP); amino substituted hydroxybenzophenones such as 2-(4-Diethylamino-2-hydroxy-benzoyl)-benzoic acid hexylester (Uvinul A plus) as described in the European Patent Publication EP 1046391; Ionic UV-A filters as described in the International Patent Publication WO2005080341 A1. Pigments such as microparticulated ZnO or TiO2 and the like. The term "microparticulated" refers to a particle size from about 5 nm to about 200 nm, particularly from about 15 nm to about 100 nm. The particles may also be coated by other metal oxides such as e.g. aluminum or zirconium oxides or by organic coatings such as e.g. polyols, methicone, aluminum stearate, alkyl silane. Such coatings are well known in the art.

As dibenzoylmethane derivatives have limited photostability, it may be desirable to photostabilize these UV-A screening agents. Thus, the term "conventional UV-A screening agent" also refers to dibenzoylmethane derivatives such as e.g. PARSOL® 1789 stabilized by, e.g. 3,3-Diphenylacrylate derivatives as described in the European Patent Publications EP 0 514 491 B1 and EP 0 780 119 A1; Benzylidene camphor derivatives as described in the U.S. Pat. No. 5,605,680; Organosiloxanes containing benzmalonate groups as described in the European Patent Publications EP 0358584 B1, EP 0538431 B1 and EP 0709080 A1.

Active ingredients which may be included in the cosmetic or dermatological preparations of the invention are for example vitamins and derivatives thereof, for example tocopherol, tocopherol acetate, ascorbic acid, ascorbyl phosphate, vitamin Q, D, and K, retinol, retinal, retinoic acid, retinol acetate, retinol palmitate, biotin, carotenoid derivatives such as beta-carotene, lycopene, astaxanthin, vegetable extracts, antibacterial ingredients, instable amino acids comprising dipeptides, oligopeptides and polypeptides such as methionine, cysteine, cystine, tryptophan, phenylalanine, tyrosine, phenols, polyphenols or flavanoids, bisabolol, allantoin, phytantriol, panthenol, AHA acids, ubiquinones such as coenzyme Q 10, ceramides, pseudoceramides, essential oils, plant extracts deoxyribonucleic acid, phytanic acid without being limited thereto.

The necessary amounts of the cosmetic and dermatological adjuvants, additives and/or additional active ingredients can, based on the desired product, easily be chosen by a person skilled in the art and will be illustrated in the examples, without being limited hereto.

In a further embodiment, the present invention relates to a personal skin care kit comprising:
i) one composition for oral intake according to the invention ("oral composition") and
ii) one product suitable for topical application to the skin ("topical composition")
wherein the oral composition and the topical composition are contained separately and the separate containers are joined together in a unitary package.

According to the present invention it is preferred if the oral composition and the topical composition are applied within a time period of 1 day, preferably within a time period of 3 hours, preferably within a time period of 1 hour.

The kits of the present invention are useful for supporting a healthy skin appearance and beauty, for supporting skin nourishment from inside the body via the blood stream (systemically), and in the case of the personal care kit also from outside the body via topical application of a cosmetic composition, for supporting a clear, pure appearance of the skin, for fostering hydration, for moisturizing the skin, for supporting the skin barrier function, for providing protection against oxidative stress, for helping to prevent and alleviate sensitive skin towards environmental stressors (wind, soaps, dry climate), for providing protection against UV-radiation and/or for providing a general anti-aging effect. The kits of the present invention are in particular suitable for promoting skin repair and/or regeneration upon healing of injuries and/or for promoting the physiological renewal process and thus for promoting an optimal health, a natural radiance and glow and/or a beautiful appearance of the skin.

The invention will now be elucidated by way of the following examples, without however being limited thereto.

EXAMPLES

Camosic acid 12-methylether of Formula I was isolated from a lipophilic extract of rosemary needles by chromatography on a RP-18 column with methanol-water in a purity >95%.

Example 1

Anti-Inflammatory Effects

The anti-inflammatory effects of carnosic acid-12-methyl ether was evaluated in activated macrophages by determining the inhibition of the synthesis of nitric oxide and/or proinflammatory prostaglandins (PG). $PGE_2$ plays a critical role in the inflammation process, while nitric oxide (NO) is a hallmark of inflammation in various chronic inflammatory diseases including various forms of arthritis, gastrointestinal diseases and metabolic syndrome.

The compound was dissolved in DMSO in concentrated form and did not contain byproducts that interfered with the assays. Final vehicle (DMSO) concentration did not exceed 0.2% v/v in the assays.

The anti-inflammatory effects of compounds was tested in cellular assays using a murine macrophage indicator cell line, RAW267.7, which was purchased from American Type Culture Collection, (ATCC) and cultured in DMEM according to the protocol provided by ATCC. Cells (~50'000/well) were seeded into flat-bottomed microtiter plates and cultured for one day. Cells were then starved in complete medium containing 0.25% fetal calf serum (FCS) (D-025). After overnight culture, medium was removed and replaced by 100 µL of D-025 containing the test compounds at twice the final concentration. Subsequently, 100 µL of D-025 containing 2 µg/ml lipopolysaccharide (LPS) was added (i.e. final LPS concentration of 1 µg/ml) and the cells were cultured for 24 hours. Substances were usually tested in a concentration range from 0.2 to 50 µM in two-fold dilution steps. Concentrations of nitrite which was generated from nitric oxide released by cells were determined by the Griess reaction (see e.g Imai et al. Biochem Biophys Res Comm, 197, 105 [1993]) using sodium nitrite as standard. Briefly, 50 µl of supernatant was mixed with Griess reagent 1 (25 µL) and Griess reagent 2 (25 µL), centrifuged and the optical density at 540 nm determined. $PGE_2$ secreted into the cell culture medium was determined by EIA obtained from Cayman Chemicals (Ann Harbor, Wis., USA) and used according to the manufacturer's instructions. $IC_{50}$ values were calculated using a two-parametric least-square fitting equation [y=A+((B-A)/(1+((C-x)^D))] for best-fit curves (Excel fit software program).

In Table 2 it is shown that all substances idiosyncratically inhibited the production of inflammatory mediators. This is indicated by $IC_{50}$ values, which vary between substances reflecting substance-specific biological potencies.

TABLE 2

| $IC_{50}$ values for single substances | | |
|---|---|---|
| Substance | $IC_{50}$ $PGE_2$ | $IC_{50}$ Nitric Oxide |
| Carnosic acid-12-methyl ether (I) | 44.4 ± 6.1 µmol/L | 3.8 ± 0.6 µmol/L |

Example 2

Influence of Carnosic Acid-12-Methyl Ether (1) on the Expression of Genes Involved in The Build-Up and Break-Down of Cartilage In articular cartilage, a delicate balance between anabolic (build-up) and catabolic (break down) events needs to be maintained in order to prevent hypertrophy and excessive degradation of extracellular matrix (ECM), respectively. The ECM is built up of collagen and proteoglycans that are the products of collagen genes, for example human collagen 1 or aggrecan genes, which are activated and expressed during anabolic processes.

Catabolic events are controlled by the expression of genes, for example those genes that encode matrix metalloproteinases (MMPs) that eventually break down collagen or proteoglycans. Of the MMPs, MMP-1, MMP-3 and MMP-13 have a major role in decomposing the ECM in cartilage degradation.

The cells were treated with IL-1β, which is one of the natural mediators that induce cartilage breakdown and is detected in substantial amounts in osteoarthritic cartilage tissues and cells derived thereof. Treatment of cells with IL-1β triggers the expression of genes that are involved in catabolic events, such as MMPs. Also, treatment of the cells with IL-1β reduces the collagen expression levels (compared to untreated cells)

Chondrocytes (SW1353; purchased from the American Tissue Culture Collection [ATCC]) were grown in cell culture medium according to the instructions from ATCC. For experimental treatments, cells were seeded into 6-well plates and cultured for two days until they reached confluence. Total cellular RNA was extracted from cultured cells and reverse-transcribed as described by Richard et al. Mol. Nutr. Food Res. 49, 431-442, 2005. Expression levels of distinct genes were determined by quantitative real-time PCR as described in Richard et al. Mol. Nutr. Food Res. 49, 431-442, 2005. Results of this experiment are shown in Table 2 below:

TABLE 3

| Effect of Carnosic acid-12-methyl ether (I) on gene expression in human chondrocyte cells. | | |
|---|---|---|
| Gene | 0 µM compound | 12.5 µM Carnosic acid12-methyl ether |
| Human MMP-1 | 100% | 94% |
| Human MMP-3 | 100% | 69% |
| Human MMP-13 | 100% | 60% |
| Human collagen II | 100% | 139% |
| Aggrecan | 100% | 123% |

Percentages indicate gene expression levels relative to cells that were treated without the compound.

Carnosic acid-12-methyl ether (1) drastically reduced the expression of genes involved in the degradation of cartilage (MMP-1, MMP-3 and MMP-13), whereas they stimulated the expression of some genes associated with the build-up of cartilage (human collagen 1, human collagen 11, aggrecan). These results suggest that the indicated that carnosic acid-12-methyl ether (1) not only prevent degradation of cartilage, but also help to regenerate cartilage tissue.

Example 3

Soft Gelatin Capsule

Soft gelatin capsules are prepared by conventional procedures providing a dose of carnosic acid 12-methylether (1) of 10 mg. A suitable daily dose is 1 to 5 capsules.

Other ingredients: glycerol. Water, gelatine, vegetable oil

Example 4

Hard Gelatin Capsule

Hard gelatin capsules are prepared by conventional procedures providing a dose of carnosic acid 12-methylether (1) of 20 mg. A suitable daily dose is 1 to 5 capsules.

Other Ingredients:
Fillers: lactose or cellulose or cellulose derivatives q.s.
Lubricant: magnesium stearate if necessary (0.5%)

Example 5

Tablet

Tablets are prepared by conventional procedures providing as active ingredient 20 mg of carnosic acid 12-methylether (I) per tablet, and as excipients microcrystalline cellulose, silicone dioxide ($SiO_2$), magnesium stearate, crospovidone NF (which is a disintegration agent) ad 500 mg.

Example 6

Soft Drink

A soft drink containing carnosic acid 12-methylether (1) may be prepared as follows: A soft drink is prepared from the following ingredients:

| ingredient | [g] |
|---|---|
| A. juice concentrates and water soluble flavours | |
| 60.3° Brix, 5.15% acidity | 657.99 |
| 43.5° Brix, 32.7% acidity | 95.96 |
| Orange flavour, water soluble | 3.43 |
| Apricot flavour, water soluble | 6.71 |
| water | 26.46 |
| B. color | |
| β-carotene 10% CWS | 0.89 |
| water | 67.65 |
| C. Acid and antioxidant | |
| Ascorbic acid | 4.11 |
| Citric acid anhydrous | 0.69 |
| water | 43.18 |
| D. stabilizers | |
| pectin | 0.20 |
| Sodium benzoate | 2.74 |
| water | 65.60 |
| E. oil soluble flavours | |
| Orange flavour, oil soluble | 0.34 |
| Orange oil distilled | 0.34 |
| F. active ingredient | |
| Carnosic acid 12-methylether (I) | Amount providing 500 mg |

Fruit juice concentrates and water soluble flavours are mixed without incorporation of air. The color is dissolved in deionized water. Ascorbic acid and citric acid are dissolved in water. Sodium benzoate is dissolved in water. The pectin is added under stirring and dissolved while boiling. The solution is cooled down. Orange oil and oil soluble flavours are premixed. The active ingredient as mentioned under F is stirred into the fruit juice concentrate mixture of A.

In order to prepare the soft drinks all components A-F are mixed together before homogenizing using a Turrax and then a high-pressure homogenizer ($p_1$=200 bar, $p_2$=50 bar).

Example 7

Dry Dog Feed Comprising Carnosic Acid 12-Methylether (I)

Commercial dry dog food (Hill's Science diet "Canine Maintenance dry" for dogs as supplied by Hill's Pet Nutrition GmbH, Liebigstrasse 2-20, D-22113) is sprayed with an aqueous ROPUFA (as supplied by DSM Nutritional Products) in an amount sufficient to administer to a subject a daily dose of 4 mg to 120 mg ROPUFA per kg body weight. Further L-ascorbic acid-monophosphate (ROVIMIX® STAY-C® 35 from DSM Nutritional Products AG, Vitamin E and beta-carotene and carnosic acid-12-methylether are incorporated in an amount sufficient to provide 30 mg ROVIMIX® STAY-C® 35/kg, and 300 IU vitamin E/kg and 280 mg beta-carotene/kg and 100 mg of carnosic acid-12-methylether in the final food composition before extruding the entire blend. The food composition is dried to contain dry matter of about 90% by weight.

Example 8

Wet Cat Food Comprising Carnosic Acid 12-Methylether (I)

Commercial wet cat food (Hill's Science diet "Feline Maintenance wet" for cats as supplied by Hill's Pet Nutrition GmbH, Liebigstrasse 2-20, D-22113) is mixed with an aqueous dispersion of ROPUFA (as supplied by DSM Nutritional Products) in an amount sufficient to administer to a subject a daily dose of 4 mg to 120 mg ROPUFA. Further L-ascorbic acid-monophosphate (ROVIMIX® STAY-C® 35 from DSM Nutritional Products AG, Vitamin E and beta-carotene and sageone are incorporated in an amount sufficient to provide 30 mg ROVIMIX® STAY-C® 35 kg, and 300 IU vitamin E/kg and 280 mg beta-carotene/kg and 200 mg/kg of sageone in the final food composition before cooking the entire blend. The food composition is dried to contain a dry matter of about 90% by weight.

Example 9

Preparation of a Dermatological Composition Comprising Carnosic Acid 12-Methylether (I) (Treatment Cream) Which May be Used for (Cosmetic) Treatment of Inflammation of the Skin Caused by Sunburn.

A treatment cream may be prepared with the following ingredients, in the following amounts:

| | Ingredients | INCI Nomenclature | % w/w |
|---|---|---|---|
| A | Glyceryl Myristate | Glyceryl Myristate | 2.00 |
| | Carnosic acid 12-methylether (I) | | 0.01-20 |
| | Cetyl Alcohol | Cetyl Alcohol | 0.50 |
| | Myritol 318 | Caprylic/Capric Triglyceride | 5.00 |
| | Crodamol DA | Diisopropyl Adipate | 5.00 |
| | Vitamin E acetate | Tocopheryl Acetate | 2.00 |
| | Butylated Hydroxytoluene | BHT | 0.05 |
| | Phenonip | Phenoxyethanol & Methylparaben & Ethyl-paraben & Propylparaben & Butylparaben | 0.60 |
| | Edeta BD | Disodium EDTA | 0.10 |
| | AMPHISOL K | Potassium Cetyl Phosphate | 2.00 |
| B | Water deionized | Aqua | ad 100 |
| | 1,2-Propylene Glycol | Propylene Glycol | 2.00 |
| | D-PANTHENOL 75 L | Panthenol | 2.00 |
| | Ethanol | Ethanol | 5.00 |
| | Allantoin | Allantoin | 0.20 |
| | Carbopol ETD 2001 | Carbomer | 0.30 |

-continued

| | Ingredients | INCI Nomenclature | % w/w |
|---|---|---|---|
| C | KOH 10% sol. | Potassium Hydroxide | 1.50 |
| D | Perfume | Perfume | q.s. |

Procedure: Heat part A) and B) to 85° C. while stirring. When homogeneous, add part B) to A) under agitation. Cool to about 45° C. while stirring. Add part C). Homogenize at 11000 rpm to achieve a small particle size. Cool to ambient temperature while stirring. Then add part D).

Example 10

O/W Sun Milk

| | Ingredients | INCI Nomenclature | % w/w |
|---|---|---|---|
| A) | PARSOL SLX | Polysilicone-15 | 6.00 |
| | Neo Heliopan AP | | 3.00 |
| | Tinosorb S | Hydrogenated Cocoglycerides | 3.00 |
| | Lanette O | Cetearyl Alcohol | 2.00 |
| | Myritol 318 | Caprylic/capric Triglyceride | 6.00 |
| | Mineral oil | Mineral oil | 2.00 |
| | Vitamin E acetate | Tocopheryl Acetate | 1.00 |
| | Prisorine 3515 | Isostearyl Alcohol | 4.00 |
| B) | Edeta BD | Disodium EDTA | 0.10 |
| | Phenonip | Phenoxyethanol & Methylparaben & Ethylparaben & Propylparaben & Butylparaben | 0.60 |
| | Amphisol K | Potassium Cetyl Phosphate | 2.00 |
| | Water deionized | Aqua | ad 100 |
| | 1,2-Propylene Glycol | Propylene Glycol | 5.00 |
| | Carbopol 981 | Carbomer | 0.30 |
| | Tinosorb M | Methylene Bis-Benzotriazolyl Tetramethylbutylphenol | 6.00 |
| | KOH 10% solution | Potassium Hydroxyde | 2.10 |
| C) | Carnosic acid 12-methylether (I) | | 0.01-20 |

Procedure: Heat part A) and B) to 85° C. while stirring. When homogeneous, add part B) to A) under agitation. Cool to ambient temperature while stirring and add part C). Homogenize to achieve a small particle size.

Example 11

Sun Milk Waterproofed

| | Ingredients | INCI Nomenclature | % w/w |
|---|---|---|---|
| A) | PARSOL SLX | Polysilicone-15 | 6.00 |
| | PARSOL 1789 | Butyl Methoxydibenzoylmethane | 2.00 |
| | PARSOL 5000 | 4-Methylbenzylidene Camphor | 4.00 |
| | Uvinul T 150 | Ethylhexyltriazone | 2.00 |
| | Silicone DC 200/350 cs | Dimethicone | 1.00 |
| | Lanette O | Cetearyl Alcohol | 2.00 |
| | Softisan 100 | Hydrogenated Coco-Glycerides | 3.00 |
| | Tegosoft TN | C12-15 Alkyl Benzoate | 6.00 |
| | Cetiol B | Dibutyl Adipate | 7.00 |
| | Vitamin E acetate | Tocopheryl Acetate | 2.00 |
| | BHT | BHT | 0.05 |
| | Edeta BD | Disodium EDTA | 0.10 |
| | Phenonip | Phenoxyethanol & Methylparaben & Ethylparaben & Propylparaben & Butylparaben | 0.60 |
| | Amphisol | Cetyl Phosphate DEA | 2.00 |
| B) | Water deionized | Aqua | ad 100 |
| | Propylene Glycol | Propylene Glycol | 5.00 |
| | Carbopol 980 | Carbomer | 0.30 |
| | KOH (10% sol.) | Potassium Hydroxide | 1.50 |

-continued

| | Ingredients | INCI Nomenclature | % w/w |
|---|---|---|---|
| C) | Carnosic acid 12-methylether (I) | | 0.01-20 |

Procedure: Heat part A) and B) to 85° C. while stirring. When homogeneous, add part B) to A) under agitation. Cool to ambient temperature while stirring and add part C). Homogenize to achieve a small particle size.

Example 12

Sun Milk for Babies and Children

| | Ingredients | INCI Nomenclature | % w/w |
|---|---|---|---|
| A) | Tegosoft TN | C12-15 Alkyl Benzoate | 5.00 |
| | Silicone 2503 Cosmetic Wax | Stearyl Dimethicone | 2.00 |
| | Cetyl Alcohol | Cetyl Alcohol | 1.00 |
| | Butylated Hydroxytoluene | BHT | 0.05 |
| | Estol GMM 3650 | Glyceryl Myristate | 4.00 |
| | Edeta BD | Disodium EDTA | 0.10 |
| | Phenonip | Phenoxyethanol & Methylparaben & Ethylparaben & Propylparaben & Butylparaben | 0.60 |
| | Amphisol A | Cetyl Phosphate | 2.00 |
| B) | Water deionized | Aqua | ad 100 |
| | Carbopol 980 | Carbomer | 0.6 |
| | Glycerine | Glycerine | 3.00 |
| | KOH sol. 10% | Potassium Hydroxide | 2.4 |
| C) | Carnosic acid 12-methylether (I) | | 0.01-20 |

Procedure: Heat part A) and B) to 85° C. while stirring. When homogeneous, add part B) to A) under agitation. Cool to ambient temperature while stirring and add part C). Homogenize to achieve a small particle size.

Example 13

High Protective Sun Milk

| | Ingredients | INCI Nomenclature | % w/w |
|---|---|---|---|
| A) | PARSOL SLX | Polysilicone-15 | 6.00 |
| | PARSOL 1789 | Butyl Methoxydibenzoylmethane | 2.00 |
| | PARSOL 5000 | 4-Methylbenzylidene Camphor | 4.00 |
| | Uvinul T 150 | | 2.00 |
| | Silicone DC 200/350 cs | Dimethicone | 1.00 |
| | Lanette O | Cetearyl Alcohol | 2.00 |
| | Softisan 100 | Hydrogenated Coco-Glycerides | 3.00 |
| | Tegosoft TN | C12-15 Alkyl Benzoate | 6.00 |
| | Cetiol B | Dibutyl Adipate | 7.00 |
| | Vitamin E acetate | Tocopheryl Acetate | 2.00 |
| | BHT | BHT | 0.05 |
| | Edeta BD | Disodium EDTA | 0.10 |
| | Phenonip | Phenoxyethanol & Methylparaben & Ethylparaben & Propylparaben & Butylparaben | 0.60 |
| | Amphisol K | Potassium Cetyl Phosphate | 2.00 |
| B) | Water deionized | Aqua | ad 100 |
| | Propylene Glycol | Propylene Glycol | 5.00 |
| | Carbopol 980 | Carbomer | 0.30 |
| | KOH (10% sol.) | Potassium Hydroxide | 1.50 |
| C) | carnosic acid 12-methylether (I) | | 0.01-20 |
| D) | Perfume | Perfume | q.s. |

Procedure: Heat part A) and B) to 85° C. while stirring. When homogeneous, add part B) to A) under agitation. Cool to ambient temperature while stirring and add part C) and D). Homogenize to achieve a small particle size.

Example 14

Water-Free Sungel

| | Ingredients | INCI Nomenclature | % w/w |
|---|---|---|---|
| A) | PARSOL MCX | Ethylhexyl Methoxycinnamate | 6.00 |
| | PARSOL 1789 | Butyl Methoxydibenzoylmethane | 4.00 |
| | PARSOL 5000 | 4-Methylbenzylidene Camphor | 4.00 |
| | Uvasorb HEB | Diethylhexyl Butamido Triazone | 1.50 |
| | Uvinul A plus | | 2.00 |
| | Vitamin E acetate | Tocopheryl Acetate | 1.50 |
| | Tegosoft TN | C12-15 Alkyl Benzoate | 9.00 |
| | Elefac I-205 | Ethylhexyldodecyl Neopentanoate | 2.00 |
| | Alcohol | Alcohol | ad 100 |
| | Isopropyl Alcohol | Isopropyl Alcohol | 20.00 |
| B) | Klucel MF | Hydroxypropylcellulose | 2.00 |
| C) | carnosic acid 12-methylether (I) | | 0.01-20 |
| D) | perfume | | q.s. |

Procedure: Mix part A) and B) while stirring. When homogeneous, add part C) and D) under agitation.

Example 15

Sun Gel

| | Ingredients | INCI Nomenclature | % w/w |
|---|---|---|---|
| A) | Pemulen TR-2 | Acrylates/C10-30 Alky Acrylate Crosspolymer | 0.60 |
| | Phenonip | Phenoxyethanol & Methylparaben & Ethylparaben & Propylparaben & Butylparaben | 0.60 |
| | Edeta BD | Disodium EDTA | 0.1 |
| | Aqua | Aqua | ad 100 |
| B) | PARSOL 1789 | Butyl Methoxydibenzoylmethane | 4.00 |
| | PARSOL 340 | Octocrylene | 3.00 |
| | Tegosoft TN | C12-15 Alkyl Benzoate | 15.00 |
| | Antaron V-216 | PVP/Hexadecene Copolymer | 1.00 |
| | Vitamin E acetate | Tocopheryl Acetate | 0.50 |
| | Butylated Hydroxytoluene | BHT | 0.05 |
| | Cremophor RH 410 | PEG-40 Hydrogenated Castor Oil | 0.50 |
| | Tris Amino | Tromethamine | 0.50 |
| C) | carnosic acid 12-methylether (I) | | 0.01-20 |
| D) | Perfume | Perfume | q.s. |

Procedure: Heat part A) and B) to 85° C. while stirring. When homogeneous, add part B) to A) under agitation. Cool to ambient temperature while stirring and add part C) and D). Homogenize to achieve a small particle size.

Example 16

High protection WO Sun Milk

| | Ingredients | INCI Nomenclature | % w/w |
|---|---|---|---|
| A) | PARSOL 1789 | Butyl Methoxydibenzoylmethane | 2.00 |
| | PARSOL 5000 | 4-Methylbenzylidene Camphor | 4.00 |
| | Uvinul T 150 | Ethylhexyl Triazone | 2.00 |
| | Uvinul TiO2 | Titanium Dioxide and Trimethoxycaprylylsilane | 5.00 |
| | Arlacel P 135 | PEG-30 Dipolyhydroxystearate | 2.00 |
| | Tegosoft TN | C12-15 Alkyl Benzoate | 5.00 |
| | Cosmacol EMI | Di-C12-13 Alkyl Malate | 6.00 |
| | Miglyol 840 | Propylene Glycol Dicaprylate/Dicaprate | 6.00 |
| | Butylated Hydroxytoluene | BHT | 0.05 |
| | Phenonip | Phenoxyethanol & Methylparaben & Ethylparaben & Propylparaben & Butylparaben | 0.60 |
| B) | Deionized water | Aqua | ad 100 |
| | Glycerin | Glycerin | 5.00 |
| | Edeta | Disodium EDTA | 0.1 |
| | NaCl | Sodium Chloride | 0.30 |
| C) | PARSOL HS | Phenylbenzyimidazole Sulphonic Acid | 4.00 |
| | Water | Aqua | 20.00 |
| | Triethanolamine 99% | Triethanolamine | 2.50 |
| D) | carnosic acid 12-methylether (I) | | 0.01-20 |
| E) | Perfume | | q.s. |

Procedure: Heat part A), B) and C) to 85° C. while stirring. When homogeneous, add part B) and C) to A) under agitation. Cool to ambient temperature while stirring and add part D) and E). Homogenize to achieve a small particle size.

Example 17

W/O Milk with Pigments

| | Ingredients | INCI Nomenclature | % w/w |
|---|---|---|---|
| A) | Cremophor WO 7 | PEG-7 Hydrogenated Castor Oil | 6.00 |
| | Elfacos ST 9 | PEG-45/Dodecyl Glycol Copolymer | 2.00 |
| | PARSOL 1789 | Butyl Methoxydibenzoylmethane | 3.00 |
| | Tinosorb S | | 5.00 |
| | PARSOL 5000 | 4-Methylbenzylidene Camphor | 4.00 |
| | microfine ZnO | Zinc Oxide | 2.00 |
| | Microcrystalline wax | Microcrystalline Wax | 2.00 |
| | Miglyol 812 | Caprylic/capric Triglyceride | 5.00 |
| | Vitamin E acetate | Tocopheryl Acetate | 1.00 |
| | Jojoba oil | *Simmondsia Chinensis* Seed Oil | 5.00 |
| | Edeta BD | Disodium EDTA | 0.10 |
| | Butylated Hydroxytoluene | BHT | 0.05 |
| | Phenonip | Phenoxyethanol & Methylparaben & Ethylparaben & Propylparaben & Butylparaben | 0.60 |
| B) | Water deionized | Aqua | ad 100 |
| | Glycerin | Glycerin | 5.00 |
| C) | Neo Heliopan AP | | 2.00 |
| | Water deionized | Aqua | 20.00 |
| | KOH 10% solution | Potassium Hydroxide | 4.00 |
| D) | carnosic acid 12-methylether (I) | | 0.01-20 |

Procedure: Heat part A), B) and C) to 85° C. while stirring. When homogeneous, add part B) and C) to A) under agitation. Cool to ambient temperature while stirring and add part D). Add perfume q.s. if desirable. Homogenize to achieve a small particle size.

Example 18

Protective Day Cream with Vitamin C

| | Ingredients | INCI Nomenclature | % w/w |
|---|---|---|---|
| A) | PARSOL SLX | Polysilicone-15 | 4.00 |
| | PARSOL 1789 | Butyl Methoxydibenzoylmethane | 1.50 |
| | Glyceryl Myristate | Glyceryl Myristate | 2.00 |

-continued

| | Ingredients | INCI Nomenclature | % w/w |
|---|---|---|---|
| | Cetyl Alcohol | Cetyl Alcohol | 0.50 |
| | Myritol 318 | Caprylic/Capric Triglyceride | 5.00 |
| | Crodamol DA | Diisopropyl Adipate | 5.00 |
| | Vitamin E acetate | Tocopheryl Acetate | 2.00 |
| | Butylated Hydroxytoluene | BHT | 0.05 |
| | Phenonip | Phenoxyethanol & Methylparaben & Ethylparaben & Propylparaben & Butylparaben | 0.60 |
| | Edeta BD | Disodium EDTA | 0.10 |
| | Amphisol K | Potassium Cetyl Phosphate | 2.00 |
| B) | Water deionized | Aqua | ad 100 |
| | 1,2-Propylene Glycol | Propylene Glycol | 2.00 |
| | D-Panthenol 75 L | Panthenol | 2.00 |
| | Ethanol | Ethanol | 5.00 |
| | Allantoin | Allantoin | 0.20 |
| | Carbopol ETD 2001 | Carbomer | 0.30 |
| | KOH 10% sol. | Potassium Hydroxide | 1.50 |
| C) | Water | Aqua | 10.00 |
| | Stay-C 50 | Sodium Ascorbyl Phosphate | 0.50 |
| D) | carnosic acid 12-methylether (I) | | 0.01-20 |
| E) | Perfume | Perfume | q.s. |

Example 19

Anti-Inflammatory Effects of Carnosic Acid-12-methyl Ether (I) on Keratinocytes During skin inflammation different cytokines induce patho-physiological changes in keratinocytes. These are reflected by increased expression of e.g. psoriasin or β-defensin. Anti-inflammatory compounds that modulate expression of these genes or their products can therefore protect keratinocytes from cytokine-induced pathogenesis.

Keratinocytes were cultured in standard medium (SFM, invitrogen #1 7005075) until they reached confluence. Culture medium was then changed to assay medium (SFM without epidermal growth factor and pituary extract) and pre-incubated with the test compound for 2 hrs. In order to stimulate the cells, a cytokine mix (see Boniface et al. J. Immunol. 178, 4615-4622, 2007) was added and the cells were cultured for 24 hrs. At the end of the experiment, cells were washed; total RNA was extracted using Trizol reagents (Sigma T9424). The expression levels of specific genes (cytokeratin 10, β-defensin (defensin-β4) and psoriasin (or S100 calcium-binding protein A7) was performed by quantitative real time PCR, using the procedure described in other examples.

The effect of carnosic acid 12-methyl ether is shown in Table 4. For two genes that reflect the shift to a patho-physiological status, the compound dose-dependently reduced the expression. This is evidence that carnosic acid 12-methyl ether strongly reduces the inflammatory processes of keratinocytes induced by cytokines.

TABLE 4

| | Gene expression (in % of stimulated cells) | |
|---|---|---|
| Treatment | β-defensin | Psoriasin |
| Unstimulated | 0 | 0 |
| Stimulated | 100 | 100 |
| Stimulated + carnosic acid 12 methyl ether (0.1 μmol/L) | 49 | 46 |
| Stimulated + carnosic acid 12 methyl ether (1.0 μmol/L) | 47 | 58 |
| Stimulated + carnosic acid 12 methyl ether (5.0 μmol/L) | 28 | 62 |

Example 20

"Ideal Skin Formula I" for Oral Consumption

Lecithin is dissolved in the ROPUFA® 75 n-3 '75'EE (ethylester, containing min. 75% n-3 fatty acid ethyl ester, stabilized with mixed tocopherol, ascorbyl palmitate and rosemary extracts; commercially available from DSM Nutritional Products AG, Kaiseraugst, Switzerland) and the beta-Carotene 30% FS, Lutein 20% FS (extracted from Tagetes erecta in Corn Oil and stabilized with DL-alpha-Tocopherol), Redivivo™ (lycopene) 10% FS (in comoil, stabilized with DL-alpha-Tocopherol) (commercially available from DSM Nutritional Products AG, Kaiseraugst, Switzerland) are added, vitamin C, Carnosic acid 12-methyl ether (1), Biotin and CoEnzyme Q10 (as ALL-Q® 10% CWS/S commercially available from DSM Nutritional Products AG, Kaiseraugst, Switzerland) are mixed in a tumbler mixer for 5 minutes. This dry powder mix is dispersed in the oily mixture of ROPUFA®, carotene and lecithin and then encapsulated in capsules according to a commonly applied procedure.

| | |
|---|---|
| Beta-carotene | 3 mg (=10 mg beta-Carotene 30% FS) |
| Lycopene (redivio ™) | 3 mg (=30 mg redivivo ™ (lycopene) 10% FS) |
| Lutein | 3 mg (=15 mg Lutein 20% FS) |
| D/L-alpha-Tocopherol-acetate | 75 mg |
| Vitamin C | 75 mg (as fine powder) |
| ROPUFA ® 75 n-3 '75'EE | 400 mg |
| Carnosic acid 12-methyl ether (I) | 100 mg |
| Biotin | 150 μg |
| CoEnzyme Q10 (ALL-Q ®) | 5 mg (=50 mg ALL-Q ® 10% CWS/S) |
| Lecithin as mixed soybean phosphatides | 25 mg |

One capsule is taken per day together with a meal.

Example 21

"Ideal Skin Formula II" for Oral Consumption

Lecithin is dissolved in the ROPUFA® 75 n-3 '75'EE (ethylester, containing min. 75% n-3 fatty acid ethyl ester, stabilized with mixed tocopherol, ascorbyl palmitate and rosemary extracts; commercially available from DSM Nutritional Products AG, Kaiseraugst, Switzerland) and the beta-Carotene 30% FS, Optisharp™ 20% FS (in cornoil stabilized with DL-alpha-Tocopherol) are added. TEAVIGO™, vitamin C, Carnosic acid 12-methyl ether (1), Biotin and CoEnzyme Q10 (as ALL-Q® 10% CWS/S commercially available from DSM Nutritional Products AG, Kaiseraugst, Switzerland) are mixed in a tumbler mixer for 5 minutes. This dry powder mix is dispersed in the oily mixture of ROPUFA®, carotene and lecithin and then encapsulated in capsules according to a commonly applied procedure.

| | |
|---|---|
| Beta-carotene | 6 mg (=20 mg beta-Carotene 30% FS) |
| Zeaxanthin | 2.0 mg (=10 mg Optisharp ™ 20% FS) |
| D/L-alpha-tocopherol-acetate | 300 mg |
| Vitamin C | 100 mg |
| TEAVIGO ™ | 150 mg |
| ROPUFA ® 75 n-3 '75'EE | 400 mg |
| Carnosic acid 12-methyl ether (I) | 100 mg |
| Biotin | 300 μg |
| CoEnzyme Q10 (ALL-Q ®) | 20 mg (=200 mg ALL-Q ® 10% CWS/S) |
| Lecithin as mixed soybean phosphatides | 40 mg |

One capsule is taken per day together with a meal.

Example 22

"A Kit for Oral Consumption"

The liquid active ingredients beta-carotene, zeaxanthin, DL-alpha-tocoherol-acetate, and ROPUFA® 75 n-3 '75'EE can be provided within a capsule whereas the solid ingredients vitamin C, Carnosic-acid 12-methyl ether, Biotin and CoQ10 are provided in the form of a tablet. The tablet may be prepared with commonly known tabletting excipients such as dry binders e.g. microcrystalline cellulose, lactose, other carbohydrates or carbohydrate derivatives like starch, sorbitol, mannitol dextrins etc. A disintegrant like croscarmelilose or crospovidone may be added in an appropriate amount, as well as a lubricant like mg-stearate or a similar compound, a behenate polyethyleneglycol, or any other lubricant.

| | Capsule |
|---|---|
| Beta-carotene | 6 mg (=20 mg beta-Carotene 30% FS) |
| Zeaxanthin | 2.0 mg (=10 mg Optisharp ™ 20% FS) |
| Carnosic acid 12-methyl ether (I) | 100 mg |
| D/L-alpha-tocopherol-acetate | 300 mg |
| ROPUFA ® 75 n-3 '75'EE | 400 mg |
| Biotin | 300 μg |
| Lecithin as mixed soybean phosphatides | 40 mg |

This oily mix is encapsulated in capsules according to a commonly applied procedure. Taken regularly, i.e. once per day, provides a clear skin appearance with natural radiance and glow

|  | Tablet |
| --- | --- |
| Vitamin C | 110 mg (as Ascorbic Acid 90% Granulation) |
| TEAVIGO ™ TG | 150 mg |
| Carnosic acid 12-methyl ether (I) | 100 mg |
| Biotin | 300 µg |
| CoEnzyme Q10 (ALL-Q ®) | 20 mg (=200 mg ALL-Q ® 10% CWS/S) |
| Microcrystalline cellulose | 300 mg |
| Lactose | 300 mg |
| Crospovidone | 35 mg |
| Mg-Stearate | 24.7 mg |

Biotin and microcrystalline cellulose is mixed in a tumbler mixer for 10 min. Then, lactose is added and the composition mixed for 10 min again. Vitamin C, TEAVIGO ™ TG, Carnosic acid-12-methyl ether, CoQ10 and Crospovidone are combined with the other ingredients and mixed for 10 min. Finally, mg-stearate is added to the other components and mixed for another 2 min. The mixture is compressed to tablets.

In order to provide the kit for oral intake according to the invention, the tablet and the capsule are individually packed in separate containers and then packed together in a unitary form.

Per day one capsule and one tablet are taken at the same time together with a meal.

Example 23

"A Personal Care Kit"

A capsule as described in example 20 or 21 is used together with an anti-ageing cream. The anti-aging cream containing the ingredients indicated below can be prepared in a manner known per se.

| Anti-aging cream O/W emulsion | |
| --- | --- |
| Ingredients | % (w/w) |
| Glyceryl Myristate | 4.00 |
| Cetyl Alcohol | 2.00 |
| Steareth-2 | 2.00 |
| Steareth-21 | 2.00 |
| Isopropyl Myristate | 5.00 |
| Caprylic/Capric Triglyceride | 8.00 |
| BHT | 0.05 |
| Dimethicone | 2.00 |
| Phenoxyethanol & Methylparaben & Ethylparaben & Butylparaben & Propylparaben & Isobutylparaben | 0.80 |
| CoEnzyme Q10 (ALL-Q ®) | 0.50 |

-continued

| Anti-aging cream O/W emulsion | |
| --- | --- |
| Ingredients | % (w/w) |
| Carnosic acid 12-methyl ether | 1.0 |
| Xanthan Gum | 0.50 |
| Disodium EDETA | 0.10 |
| Propylene Glycol | 4.00 |
| Water | Ad 100 |

In order to provide the personal care kit according to the invention, the capsule and the anti-ageing cream are individually packed in separate containers and then packed together in a unitary form. The anti-ageing cream is applied once a day. One capsule is taken per day together with a meal.

The invention claimed is:

1. A method for treatment of an inflammatory disorder in animals including humans, said inflammatory disorder selected from the group consisting of an inflammatory joint disorder and an inflammatory skin condition,
   said method comprising the step of administering an effective amount of carnosic acid-12-methyl ether to animals including humans, which are in need thereof.
2. The method according to claim 1, wherein the inflammatory joint disorder is arthritis.
3. The method according to claim 1, wherein the inflammatory disorder is an inflammatory skin condition.
4. The method according to claim 1 wherein carnosic acid-12-methyl ether is comprised in a plant extract in an amount of at least 30 weight-%.

* * * * *